US 6,645,167 B1

(12) United States Patent
Whalen, II et al.

(10) Patent No.: US 6,645,167 B1
(45) Date of Patent: Nov. 11, 2003

(54) METHODS FOR EMBOLIZING VASCULAR SITES WITH AN EMBOLIZING COMPOSITION

(75) Inventors: Thomas J. Whalen, II, Encinitas, CA (US); Chinh Ngoc Tran, Mission Viejo, CA (US); Douglas Ray Hayman, Mission Viejo, CA (US); Noah Michael Roth, Irvine, CA (US); Jacques Moret, Les Bordes (FR); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/574,500

(22) Filed: May 19, 2000

Related U.S. Application Data
(60) Provisional application No. 60/135,222, filed on May 21, 1999, and provisional application No. 60/135,289, filed on May 21, 1999.

(51) Int. Cl.$^7$ ............................. A61F 2/00; A61M 1/00; A61M 29/00
(52) U.S. Cl. ...................... 604/28; 604/96.01; 523/113; 424/423
(58) Field of Search ..................... 112/241; 424/423, 424/484, 422, 499, 264, 507, 28, 9.41; 604/891.1, 96.01, 264, 49, 504, 28; 514/772.4, 529; 128/898; 606/191, 159, 170

(56) References Cited

U.S. PATENT DOCUMENTS

| | | | |
|---|---|---|---|
| 4,938,763 A | | 7/1990 | Dunn et al. |
| 5,580,568 A | | 12/1996 | Greff et al. |
| 5,650,447 A | | 7/1997 | Keefer et al. |
| 5,667,767 A | * | 9/1997 | Greff et al. .................. 112/241 |
| 5,695,480 A | | 12/1997 | Evans et al. |
| 5,830,178 A | | 11/1998 | Jones et al. |
| 5,888,546 A | | 3/1999 | Ji et al. |
| 5,894,022 A | | 4/1999 | Ji et al. |
| 6,335,384 B1 | * | 1/2002 | Evans et al. .................. 424/423 |

FOREIGN PATENT DOCUMENTS

| | | |
|---|---|---|
| WO | WO 90/03768 | 4/1990 |
| WO | WO 98/04312 | 2/1998 |
| WO | WO 99/20326 | 4/1999 |

OTHER PUBLICATIONS

Mandai, et al., "Direct Thrombosis of Aneurysms with Cellulose Acetate Polymer", *J. Neurosurg.*, 77:497–500 (1992).
Kinugasa, et al., "Direct Thrombosis of Aneurysms with Cellulose Acetate Polymer", *J. Neurosurg.*, 77:501–507 (1992).
Casarett and Doull's *Toxicology*, Amdur et al., Editors, Pergamon Press, New York, pp. 661–664 (1975).
Kinugasa, et al., "Early Treatment of Subarachnoid Hemorrhage After Preventing Rerupture of an Aneurysm", *J. Neurosurg.*, 83:34–41 (1995).
Kinugasa, et al., "Prophylactic Thrombosis to Prevent New Bleeding and to Delay Aneurysm Surgery", *Neurosurg.*, 36:661 (1995).

(List continued on next page.)

Primary Examiner—Michael J. Hayes
Assistant Examiner—Roz Ghafoorian (57) ABSTRACT

Disclosed are novel methods for embolizing blood vessels comprising delivering, via a catheter, an embolic composition comprising a biocompatible polymer, a biocompatible water insoluble contrast agent, and a biocompatible solvent. In one embodiment, the method is conducted during a single surgical procedure whereby a flow-arresting device is positioned and activated at the vascular site to be embolized, the embolic composition is injected, and the flow-arresting device is deactivated. In another embodiment, the method is conducted during a single surgical procedure whereby two embolic compositions, situated adjacent to one another, are injected at the vascular site to be embolized.

7 Claims, 3 Drawing Sheets

OTHER PUBLICATIONS

Taki, et al., "Selection and Combinations of Various Endovascular Techniques in the Treatment of Giant Aneurysms", *J. Neurosurg.*, 77:37–42 (1992).

Moret, et al., "The "Remodeling Technique" in the Treatment of Wide Neck Intracranial Aneurysms", *Interventional Neuroradiology,* 3: 21–35 (1997).

Aletich, et al., "The Remodeling Technique of Balloon–Assisted Guglielmi Detachable Coil Placement in Wide–Necked Anuerysms: Experience at the University of Illinois at Chicago", *J. Neurosurg,* 93: 388–396 (2000).

Nelson, et al., "Balloon–assisted Coil Embolization of Wide–Necked Aneurysms of the Internal Carotid Artery: Medium–term Angiographic and Clinical Follow–up in 22 Patients", *Am. J. Neuroradiol.,* 22: 19–26 (2001).

Malek, et al., "Balloon–assist Technique for Endovascular Coil Embolization of Geometrically Difficult Intracranial Aneurysm", *Neurosurgery,* 46(6): 1397–1407 (2000).

Riina, et al. "Future Endovascular Management of Cerebral Aneurysms", *Neurosurgery Clinics of North America, 9*(4): 917–921 (1998).

Weill, et al., "Giant Aneurysms of the Middle Cerebral Artery Trifurcation Treated with Extracranial–Intracranial Arterial Bypass and Endovascular Occlusion", *J. Neurosurg., 89*: 474–478 (1998).

Pierot, et al., "Endovascular Treatment of Post–Traumatic Complex Carotid–Cavernous Fistulas, Using the Arterial Approach", *J. Neuroradiol., 19*: 79–87 (1992) (document presented in both English and French).

Cognard, et al., "Treatment of Distal Aneurysms of the Cerebellar Arteries by Intraaneurysmal Injection of Glue", *Am. J. Neuroradiol., 20*: 780–784 (1999).

* cited by examiner

METHODS FOR EMBOLIZING VASCULAR SITES WITH AN EMBOLIZING COMPOSITION

CROSS-REFERENCE TO RELATED APPLICATIONS

This application claims the benefit of U.S. Provisional Patent Application Serial No. 60/135,222, filed May 21, 1999, and of U.S. Provisional Patent Application Serial No. 60/135,289, filed May 21, 1999, which applications are incorporated herein by reference in their entirety.

BACKGROUND OF THE INVENTION

1. Field of the Invention

This invention is directed to novel methods for embolizing blood vessels which are particularly suited for treating aneurysms, AVM and high flow fistulas. In one embodiment, the compositions employed in the methods of this invention comprise a biocompatible polymer, a biocompatible solvent and a biocompatible contrast agent wherein the viscosity of this composition is at least about 150 cSt at 40° C. and, preferably, at least 200 cSt at 40° C.

2. References

The following publications are cited in this application as superscript numbers:

[1] Mandai, et al., "Direct Thrombosis of Aneurysms with Cellulose Acetate Polymer", *J. Neurosurg.*, 77:497–500 (1992)

[2] Kinugasa, et al., "Direct Thrombosis of Aneurysms with Cellulose Acetate Polymer", *J. Neurosurg.*, 11:501–507 (1992)

[3] Casarett and Doull's *Toxicology*, Amdur et al., Editors, Pergamon Press, New York, pp. 661–664 (1975)

[4] Greff, et al., U.S. Pat. No. 5,667,767 for "Novel Compositions for Use in Embolizing Blood Vessels", issued Sep. 16, 1997.

[5] Greff, et al., U.S. Pat. No. 5,580,568 for "Cellulose Diacetate Compositions for Use in Embolizing Blood Vessels", issued Dec. 3, 1996.

[6] Kinugasa, et al., "Early Treatment of Subarachnoid Hemorrhage After Preventing Rerupture of an Aneurysm", *J. Neurosurg.*, 8:34–41 (1995)

[7] Kinugasa, et al., "Prophylactic Thrombosis to Prevent New Bleeding and to Delay Aneurysm Surgery", *Neurosurg.*, 36:661 (1995)

[8] Taki, et al., "Selection and Combination of Various Endovascular Techniques in the Treatment of Giant Aneurysms", *J. Neurosurg.*, 27:37–42 (1992)

[9] Evans, et al., U.S. patent application Ser. No. 08/655,822 for "Novel Compositions for Use in Embolizing Blood Vessels", filed May 31, 1996

[10] Dunn, et al., U.S. Pat. No. 4,938,763 for "Biodegradable In-Situ Forming Implants and Methods of Producing Same", issued Jul. 3, 1990

[11] Greff, et al., U.S. Pat. No. 5,695,480 for "Novel Embolizing Compositions", issued Dec. 9, 1997

[12] Greff, et al., U.S. Pat. No. 5,830,178 for "Novel Methods for Embolizing Vascular Sites with an Embolizing Composition Comprising Dimethylsulfoxide, issued Nov. 3, 1998.

All of the above references are herein incorporated by reference in their entirety to the same extent as if each individual reference was specifically and individually indicated to be incorporated herein by reference in its entirety.

3. State of the Art

Embolization of blood vessels is conducted for a variety of purposes including the treatment of tumors, the treatment of lesions such as aneurysms, uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuroendovascular intervention including the treatment of otherwise inoperable lesions. Specifically, development of microcatheters and guide wires capable of providing access to vessels as small as 1 mm in diameter allows for the endovascular treatment of many lesions.

Embolizing compositions heretofore disclosed in the art include those comprising a biocompatible polymer, a biocompatible solvent and a contrast agent which allowed visualization of the in vivo delivery of the composition via fluoroscopy.[1-8] Such compositions typically contain no more than about 8 weight percent of biocompatible polymer based on the weight of the total composition.

Endovascular treatment regimens preferably include the use of a water insoluble, radiopaque contrast agent in the embolizing compositions in order that the physician can visualize delivery of the composition to the vascular site via conventional techniques such as fluoroscopy.[1-8] Additionally, the use of water insoluble contrast agents is beneficial during post treatment procedures to visualize the embolized mass during, for example, surgery or to monitor the disease condition and/or for retreatment purposes. Visualization is particularly necessary when using catheter delivery techniques in order to ensure both that the composition is being delivered to the intended vascular site and that the requisite amount of composition is delivered. The latter requirement is particularly critical in the treatment of aneurysms where only the aneurysm sac is intended to be filled while leaving the adjoining blood vessel unaffected. Accordingly, in such treatments, the amount of embolic composition delivered is selected to substantially fill but not overflow the aneurysm sac. If less than this amount of embolic composition is delivered to the aneurysm sac, the patient will be left with an active aneurysm which, in some cases, may grow or enlarge. If more than this amount of embolic composition is delivered, the composition will overflow into the adjoining blood vessel which can then embolize this blood vessel as well as the aneurysm. In the case where the affected blood vessel is in or leads to a critical body organ, e.g., the brain, permanent damage due to ischemia will result.

When delivered by catheter, the embolic compositions preferably comprise a biocompatible solvent, a biocompatible polymer and the water insoluble contrast agent. The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The water insoluble contrast agent is suspended in the composition and, as above, permits the physician to fluoroscopically visualize catheter delivery of this composition. Upon contact with the blood or other body fluid, the biocompatible solvent dissipates from the embolic composition whereupon the biocompatible polymer precipitates in the presence of the water insoluble contrast agent and embolizes the blood vessel.

In practice, complications in this procedure have hindered the delivery of the embolic composition into vascular sites. For example, the use of a flow arresting device to limit blood flow during aneurysm treatment by injection of an embolic composition from a catheter has been heretofore suggested.[11] However, there are severe limitations placed on the use of such devices in combination with embolic compositions delivered via catheters. For example, in situ solidification of these composition is facilitated by blood transport of the biocompatible solvent away from the growing precipitate. However, a flow arresting device limits the amount of blood flow in the area adjacent the precipitate which, in turn, hinders further precipitate formation. Moreover, blood flow can be arrested for only a short period of time prior to the onset of tissue damage due to ischemia.

In addition, reproducible formation and control of precipitate formed from the embolic composition at the desired vascular site is critical to effectively treat vascular disorders. While techniques heretofore disclosed in the art provide an adequate level of reproducibility[12], new methods which enhance the reproducibility of these techniques would be of great value.

In view of the above, the art is in search of improved embolization techniques.

SUMMARY OF THE INVENTION

This invention is directed to novel methods for embolizing blood vessels which are particularly suited for treating aneurysms, AVM's and high flow fistulas. These methods, either singularly or in combination, permit the facile delivery of liquid embolic compositions to vascular sites while overcoming one or more of the problems heretofore associated with vascular embolization by use of these compositions. These methods, either singularly or in combination, further permit the controlled, reproducible formation of an embolic precipitate at the vascular site.

In one aspect, the invention is directed to a method for embolizing a vascular site comprising an opening that is in communication with a vascular vessel by delivering via a catheter to said vascular site a composition comprising (1) a biocompatible polymer; (2) a biocompatible water insoluble contrast agent; and (3) a biocompatible solvent, said method includes:

(a) positioning the distal end of a delivery catheter in said vascular site wherein the delivery catheter is connected to a source of said composition and whereby said composition can be injected into the vascular site through the delivery catheter;

(b) positioning a flow arresting device (e.g., balloon) at the vascular site to be embolized;

(c) activating the flow arresting device (i.e., a device that either controls or reduces blood flow through a vessel) at the vascular site to be embolized such that the activated device substantially arrests blood flow through the vascular site; and (d) injecting said composition into the vascular site;

(e) deactivating said flow arresting device to permit sufficient blood flow through said vascular site to be embolized such that removal of the biocompatible solvent is facilitated and oxygenated blood is delivered to the tissue distal to said flow arresting device; and (f) repeating procedures (c)–(e) at least once and as necessary to effect embolization of said vascular site.

Preferably, step (c) comprises inflating a balloon so that the inflated balloon has a diameter that is greater than the inner diameter of the vascular vessel. In one embodiment, the balloon is inflated to a diameter that is about 100% to 130% of the inner diameter of the vascular vessel, and more preferably about 115%.

In another embodiment, after procedure (d), the balloon is deflated until its diameter is about 10% to 90% of the inner diameter of the vascular vessel and allowing at least some of the biocompatible solvent to be removed from the vascular site by entrainment in bodily fluid, e.g., blood. Preferably the diameter is reduced to about 20–25% of the diameter of the vascular vessel.

In another aspect the invention is directed to a method for embolizing a vascular site comprising an opening that is in communication with a vascular vessel by delivering via a catheter into said vascular site a first embolic composition and then a second embolic composition wherein each embolic composition comprises (1) a biocompatible polymer; (2) a biocompatible water insoluble contrast agent; and (3) a biocompatible solvent, said method includes:

(a) positioning the distal end of a delivery catheter in said vascular site wherein the delivery catheter defines a channel that contains first embolic composition and the second embolic composition wherein the first embolic composition is situated adjacent the distal end and the second embolic composition is situated adjacent to the first embolic composition and whereby said first and second embolic compositions can be injected into the vascular site through the delivery catheter and wherein the first embolic composition has a higher concentration or viscosity of biocompatible polymer than the second embolic composition;

(b) injecting the first embolic composition in said vascular site whereby substantially no axial mixing of the first and second embolic compositions occurs in the channel and, thereafter, (c) injecting the second embolic composition into the vascular site.

As is apparent, the technique is applicable to injecting two or more formulations.

In one embodiment, procedure (b) comprises applying a first force into the channel to inject said first embolic composition into the vascular site and, procedure (c) comprises applying a second force into the channel to inject said second embolic composition into the vascular site wherein the first force is greater than the second force.

In another embodiment, following procedure (b) the first embolic composition forms a nidus (kernel) in the vascular site and following procedure (c) the second embolic forms a precipitate that emanates from the nidus, wherein the precipitate embolizes the vascular site.

In a further aspect, the invention is directed to a method for embolizing a vascular site comprising an opening that is in communication with said site by delivering via a catheter into said site a composition comprising (1) a biocompatible polymer; (2) a biocompatible water insoluble contrast agent; and (3) a biocompatible solvent, said method includes:

(a) positioning the distal end of a delivery catheter into the vascular site wherein the delivery catheter is connected to a source of said composition and whereby said composition can be injected into the vascular site through the delivery catheter;

(b) positioning a flow arresting device at the vascular site to be embolized;

(c) injecting the biocompatible solvent (e.g., DMSO) into the catheter to fill the lumen of said catheter followed by injecting a first amount of said composition into said catheter thereby at least a portion of said biocompatible solvent is ejected from said catheter into the vascular site and washed downstream therefrom;

(d) activating a flow arresting device at the vascular site so that the activated device substantially seals the opening;

(e) injecting the first amount of said composition from said catheter into the vascular site to form a nidus (kernal) of the embolizing composition;

(f) inactivating the flow arresting device;

(g) determining the volume of the vascular site that has been embolized; and (h) repeating procedures (e), (f), and (g) as needed to embolize the vascular site.

In the above method, repeating procedure (e), (f) and (g) is preferably done at least one.

In one embodiment, prior to procedure (c) said method further comprises:

(i) inflating a balloon to a first size in the vascular vessel so that the opening is substantially sealed; and, before procedure (e)

(j) deflating the balloon.

In another embodiment, procedure (c) comprises:

(1) filling the catheter with biocompatible solvent (e.g., DMSO);

(2) connecting the catheter to the source of the embolic composition; and (3) injecting the first amount of composition into the vascular vessel.

In other preferred embodiments: (1) the vascular site has an upper surface (fundus) and a base at the opening wherein the base and fundus are spaced apart by a distance D and procedure (a) comprises positioning the distal end of the catheter a distance of about one-third D from the upper surface, (2) procedure (c) takes place while the flow arresting device is deactivated and comprises injecting an amount of the embolic composition into the vascular site and wherein following procedure (c), the method comprises allowing the biocompatible solvent to be flushed out of the vascular site, (3) procedure (e) comprises injecting an amount of the embolic composition and procedure (f) comprises deactivating the device to allow perfusion, and/or (4) procedure (e) comprises injecting for a time period to permit perfusion and procedure (f) comprises deactivating the device to allow perfusion.

In yet another aspect, the invention is directed to a method for embolizing a vascular site comprising an opening that is in communication with a vascular vessel by delivering via a catheter to said vascular site a composition comprising (1) a biocompatible polymer; (2) a biocompatible water insoluble contrast agent; and (3) a biocompatible solvent, said method includes:

(a) positioning the distal end of a delivery catheter in said vascular site wherein the delivery catheter is connected to a source of said composition and whereby said composition can be injected into the vascular site through the delivery catheter;

(b) activating a flow arresting device in the vascular vessel so that the activated device substantially seals the opening and does not occlude the delivery catheter; and (c) injecting a single mass (bulk) of said composition into the vascular site wherein the single mass is sufficient to substantially fill the vascular site.

In one embodiment, the method further comprises the procedure of measuring the volume of the vascular site before injecting the single mass in said site.

In other embodiments (1) the volume of the single mass that is injected is substantially equal to that of the vascular site, and/or (2) the activated device is kept inflated for a sufficient amount of time until the biocompatible polymer has formed a precipitate at the vascular site.

In yet another aspect the invention is directed to a method for embolizing a vascular site comprising an opening that is in communication with a vascular vessel by delivering via a catheter into said vascular site an embolizing composition including (1) a biocompatible polymer; (2) a biocompatible water insoluble contrast agent; and (3) a biocompatible solvent, said method includes:

(a) positioning the distal end of a delivery catheter into the vascular site wherein the delivery catheter is connected to a source of a first embolizing composition and second embolizing composition and whereby said first and second embolizing compositions can be injected into the vascular site through the delivery catheter and wherein the first embolizing composition has a higher concentration or concentration of biocompatible polymer than the second embolizing composition;

(b) injecting said first embolizing composition into said vascular site to form a nidus (kernel) of the first embolizing composition; and, thereafter, (c) injecting said second embolizing composition into said vascular site to form a precipitate emanating from the nidus that embolizes the vascular site.

In other embodiments (1) the method prior to procedure (a) further comprises inflating a balloon in the vascular vessel so that the balloon when inflated seals the opening and does not occlude the delivery catheter, and/or (2) the balloon when inflated has a diameter that is greater than the inner diameter of the vascular vessel.

Preferably, the methods employ a device to connect the delivery system (e.g., catheter liner) and the injector (e.g., syringe) to create a blunt interface between delivered liquids.

Preferably, and as noted above, when treating aneurysms, the distal end of the catheter is placed approximately ⅓ from the top of aneurysm.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE INVENTION

This invention is directed to novel compositions for embolizing blood vessels which are particularly suited for treating vascular lesions via catheter delivery of the composition.

However, prior to discussing this invention in further detail, the following terms will first be defined:

The term "embolizing" refers to a process wherein a material is injected to a blood vessel which, in the case of, for example, aneurysms, fills or plugs the aneurysm sac and/or encourages clot formation so that blood flow into the aneurysm ceases, in the case of high flow AVM's forms a plug or clot to control/reroute blood flow to permit proper tissue perfusion, and, in the case of a vascular site, fills the vascular site to prevent blood flow there through. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to plymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art. For example, Dunn, et al.[10] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 206,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble.

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 μm or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of sample, ethyl lactate, dimethylsulfoxide, analogues/homologues of dimethysulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

Compositions

The polymer compositions employed in this invention are prepared by conventional methods whereby each of the components is added and the resulting composition mixed together until the overall composition is substantially homogeneous.

For example, these compositions can be prepared by adding sufficient amounts of the biocompatible polymer to the biocompatible solvent to achieve the effective concentration for the polymer composition. Preferably, the polymer composition will comprise from about 2 to about 50 weight percent of the biocompatible polymer composition based on the total weight of the polymer composition and more preferably from about 12 to about 50 weight percent. If necessary, gentle heating and stirring can be used to effect dissolution of the biocompatible polymer into the biocompatible solvent, e.g., 12 hours at 50° C. for EVOH in DMSO.

Sufficient amounts of the contrast agent are then added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 weight percent. Insofar as water insoluble contrast agents are not soluble in the biocompatible solvent, stirring is employed to effect homogeneity of the resulting suspension for compositions employing such constrast agents.

In order to enhance formation of the suspension, the particle size of water insoluble contrast agents is preferably maintained at about 10 $\mu$m or less and more preferably at from about 1 to about 5 $\mu$m (e.g., an average size of about 2 $\mu$m). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting solution or suspension is conducted as necessary to achieve homogeneity of the composition. Preferably, mixing/stirring of the composition is conducted under an anhydrous atmosphere at ambient pressure. The resulting composition is heat sterilized and then stored preferably in sealed bottles or vials until needed.

Each of the polymers recited herein is commercially available but can also be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

The embolic compositions used in the methods of this invention preferably are high viscosity compositions having a viscosity of at least 150 cSt at 40° C., more preferably, at least 200 cSt at 40° C. and even more preferably, at least 500 cSt at 40° C.

In specific preferred embodiments, the embolic compositions used in the methods of this invention have a viscosity which ranges from about 200 to 40,000 cSt at 40° C., more preferably from about 500 to 40,000 cSt at 40° C. In another embodiment, the viscosity ranges from about 500 to 5,000 cSt at 40° C. Examples of such high viscosity compositions are set forth in U.S. patent application Ser. No. 09/574,379, concurrently filed herewith as Attorney Docket No. 018413-257, entitled, "Novel High Viscosity Embolizing Compositions," which application is incorporated herein by reference in its entirety.

One preferred embolizing composition for use in the methods of this invention comprises, for example, a biocompatible polymer at a concentration of from about 12 to about 50 weight percent; a biocompatible contrast agent at a concentration of from about 10 to about 40 weight percent; and a biocompatible solvent from about 10 to 78 weight percent wherein the weight percent of the biocompatible polymer, contrast agent and biocompatible solvent is based on the total weight of the complete composition and further wherein the composition has a viscosity of at least about 150 cSt at 40° C. and preferably at least 200 cSt at 40° C.

Another preferred embolizing composition for use in the methods of this invention comprises a biocompatible polymer at a concentration of from about 2 to 50 weight percent; a biocompatible contrast agent at a concentration of from about 10 to about 40 weight percent; and a biocompatible solvent from about 10 to 88 weight percent wherein the weight percent of the biocompatible polymer, contrast agent and biocompatible solvent is based on the total weight of the complete composition and further wherein the composition has a viscosity of at least about 150 cSt at 40° C. and preferably at least 200 cSt at 40° C.

Preferably in this particular composition, the concentration of the polymer ranges from 6 to 50 weight percent and more preferably 8 to 30 weight percent.

Methods

The compositions described above can then be employed in methods for the catheter assisted embolization of mammalian blood vessels. In such methods, a sufficient amount of this composition is introduced into the selected blood vessel via a catheter delivery means under fluoroscopy so that upon precipitation of the polymer, the blood vessel is embolized. The particular amount of embolizing composition employed is dictated by the total volume of the vasculature to be embolized, the concentration of polymer in the composition, the rate of precipitation (solids formation) of the polymer, etc. Such factors are well within the skill of the art.

One particularly preferred method for catheter delivery of the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

In a preferred embodiment, the microcatheter is employed in combination with a threaded syringe which has a threaded plunger which is operable as a conventional syringe for aspiration of the embolic composition and then is used in a threaded manner for delivery of the embolic composition. The threaded syringe may also include a tactile or audible indication of delivery which allows clinician to monitor delivery of the embolic composition without looking at the syringe. The catheter for delivery of the embolic compositions preferably has a burst strength of 100 psi or greater, and more preferably 200 psi or greater, and still more preferably 1000 psi or greater. In order to prevent catheter burst, the threaded syringe may be provided with a force release mechanism which prevents the clinician from applying pressures above the catheter burst strength. As an alternative delivery means to the threaded syringe, a syringe pump may be used.

When a water insoluble contrast agent is employed, the composition delivered in vivo should have this agent uniformly suspended therein. Preferably, such a uniform suspension is achieved by heating/mixing the composition at a temperature of above 40° C. which ensures formation of a uniform suspension and then this heated/mixed composition is transferred while maintaining its temperature above room temperature and preferably above 40° C. into the catheter for in vivo delivery.

Specifically, a uniform suspension is achieved by mixing the compositions at a temperature above about 40° C., preferably from above about 40° C. to about 90° C., and more preferably from about 50° C. to about 70° C. The particular temperature employed should be sufficiently high to ensure adequate mixing of the composition.

In a particularly preferred embodiment, the composition is heated for a period of time from at least about 3 to about 20 minutes and preferably from about 5–10 minutes to facilitate formation of a uniform suspension. In some cases, the formation of a uniform suspension requires that the heated composition be placed in a suitable mixer, e.g., vortex mixer, and is mixed until the suspension is homogeneous. In this case, after formation of the homogenous suspension via the mixer, the composition is preferably reheated to a temperature of from above about 40° C. to about 90° C. and preferably from about 50° C. to about 70° C. The specific temperature employed for heating is selected relative to the biocompatible solvent and biocompatible polymer employed. Such selections are well within the skill of the art.

In either case, the heated composition is then transferred preferably via a syringe and delivered into the catheter under conditions wherein the temperature of the composition is above room temperature and preferably above about 40° C. In one preferred embodiment, the conditions which effect such transfer are rapid transfer (e.g., transfer occurs within 2 minutes of heating cessation) of the composition to the catheter.

Surprisingly, the heated composition maintains both a uniform suspension and ease of delivery during catheter injection into a vascular site in a mammal and, when ejected at the distal end of the catheter, there is no evidence of trauma to this site. See, for example, U.S. patent application Ser. No. 09/574,963, now U.S. Pat. No. 6,454,738, filed concurrently, and entitled, "Methods for Delivering In Vivo Uniform Dispersed Embolic Compositions of High Viscosity,"

Figure 10:
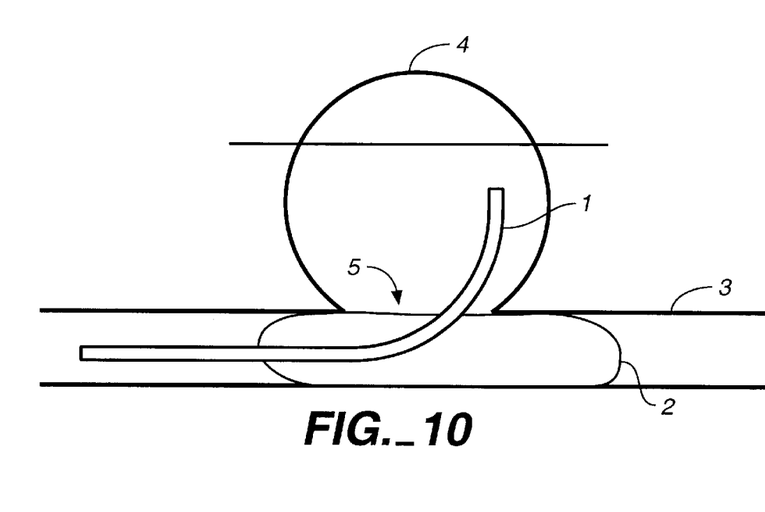
FIG. 10 is a cross-sectioned view of a side-wall aneurysm.

The preferred delivery techniques will be described in treating aneurysm but it is understood that the techniques are applicable treating vascular sites in general. As shown in FIG. 10, vascular vessel 3 has an opening 5 that is connected to a vascular sac that forms the aneurysm. The top of the sac is typically referred as the fundus 4 and the base of the sac at the opening is the neck.

Standard procedures can be employed to position the distal (i.e., tip) of delivery catheter 1 into the sac. One method of securing the delivery catheter 1 in place is during the embolization procedure is to employ a occluding or flow arresting devices such as inflatable balloon 2.

The proximal end of the delivery catheter is connected to one or more syringes. Multiple syringes each containing different embolizing compositions can be employed to load the compositions into the channel of the delivery catheter. For example, in the "stack" method two compositions comprising different polymer concentrations are used. The first formulation to be injected into the vascular site preferably has a higher polymer concentration than that of the second although, it is contemplated that the concentration of the first polymer can be less than the concentration of the second polymer. Given the length of the delivery catheter, a preferred method of injecting both the first and second compositions is load the compositions in the catheter in tandem or series thereby forming a "stack" in the channel of the catheter. Thereafter, force is applied to inject the compositions.

Preferably an interface needle, which is described herein, is employed to connect the luer of the catheter to the syringe. This interface needle creates a blunt flow pattern so that the embolizing composition entering into the catheter channel from the syringe remain uniform, that is, the compositions do not mix but remain as discrete volumes.

A. Pulse Injection

This technique is suited for delivering "stack" compositions wherein two or more different formulations are injected. In particular, it can be employed to deliver a high viscosity embolizing formulation at the distal tip of a delivery system and the formation of an initial nidus within the aneurysm during a balloon assisted embolization technique.

In one embodiment, a small quantity of a high viscosity solution of the composition (e.g., 0.025 cc of an embolic composition comprising 30% polymer) is injected into the delivery system followed by a lower viscosity material (e.g., a similar composition comprising only 12% to 14% of the same polymer). A hard pulse (1–3 lbs.) methodology is used to provide a sufficient pressure head to advance the high viscosity material to the tip of the delivery system followed by the lower viscosity material. Once the high viscosity material has reached the tip of the delivery system as visualized by fluoroscopy, a soft pulse action (0.1–0.5 lbs.) is used to produce an initial nidus of the composition.

This procedure allows for reproducible precipitate formation at the vascular site thereby reducing the likelihood of precipitate formation at unintended sites.

B. Controlled Embolization of an Aneurysm

This technique comprises a procedure for injecting an embolic composition into a vascular site in a controlled manner. The method allows for nidus formation and delivery of a controlled amount the composition to specific location to complete the embolization. This technique is particularly suited for use of an interface needle and a threaded syringe both of which are described herein.

The method as described in the following protocol for treating a representative aneurysm having a vascular volume of about 1 cc. As is apparent, the volume of materials used herein can be adjusted accordingly, for instance, to different size aneurysms. Further, the time periods involved will range depending on the site of the aneurysm, e.g, brain, and the patient's condition.

Aneurysm Procedure

1. Place balloon catheter at the vascular site.
2. Place distal tip of the delivery catheter tip just below top ⅓ of fundus.
3. Inflate the balloon until the inflated balloon substantially seals or bridges the opening of the aneurysm.
4. Record inflation volume.
5. Flush delivery catheter with about saline, e.g., 5 cc .
6. Fill dead space of delivery catheter with DMSO, e.g., 0.25 cc.
7. Inject a desired amount of embolizing composition, e.g., 0.20 cc into the delivery catheter channel while balloon is deflated. This may take about 40 seconds.
8. Stop injection and wait until the DMSO has been sufficiently flushed from the site, e.g., 1 minute.
9. Inflate balloon preferably to the volume determined in procedure 3.
10. Slowly inject the embolizing composition until a nidus is formed in the sac of the aneurysm as visualized by fluoroscopy.
11. Injection of the composition should take place within a safe period of time (e.g., for no more than 2 minutes or 0.2 cc). This time period will depend on the location of the aneurysm (e.g., brain) and other factors.
12. The balloon also should not be inflated for extensive periods of time for similar reasons. For instance, the inflation period should be no longer than 5 minutes.
13. Completely deflate balloon and wait for sufficient amount of time to allow for perfusion, e.g., blood flow. This may be for example 1–2 minutes.
14. A contrasting agent can be used during the procedure as needed to determine percent of aneurysm or vascular fill.
15. Repeat procedures 12–16 until embolization is complete.
16. Following treatment, the delivery catheter is detached:
    17.1 Leave balloon deflated for a sufficient amount of time, e.g, 10 minutes, to permit solidification of the embolizing composition.
    17.2 Aspirate the syringe (e.g., 0.20 cc).
    17.3 Remove slack from the delivery catheter. Detach with quick pull (with balloon inflated). Catheter will detach.

C. Embolization "Stack" Method

This technique enables the repeatable formation of a nidus of embolizing composition within an aneurysm followed by uniform embolization to create a dense packing.

In one embodiment, this method permits the selective delivery of various formulations of embolizing composition into an aneurysm within one procedure and same delivery system. By this method, it is possible to fill the aneurysm with embolizing composition while minimizing the presence of crevices and/or voids within the cast.

The "stack" method first injects a more viscous solution of embolizing composition as the primary injection formulation which allows for quicker solidification and thus a nidus formation. Once the nidus has formed the reminder of the aneurysm can be filed with a lower viscosity material. The second and any subsequent injection are of a higher volume. The primary indication of use is in conjunction with a balloon assisted embolization technique.

In a preferred embodiment, a 0.025 cc injection of an embolizing composition of either a 30% or 40% EVOH was followed by an injection of a 12% composition appears to obtain good results.

In another embodiment, a pulse injection of 30% embolizing composition followed by 14% composition appears to facilitate the formation of a nidus within the aneurysm.

D. Solitary Embolization Injection

This technique applies a quick, safe, and uniform force to delivery an embolization composition. An important result is the improvement in the morphology of the embolization (i.e., the cross sectional structure and capacity to fill small crevasses.)

With this procedure, the distal tip of a delivery system is placed within and aneurysm and the neck (i.e., opening) of the aneurysm is sealed using an inflation balloon. Thereafter a single bulk (mass) injection of embolizing composition, preferably equal in volume to the internal space of the aneurysm, is injected into the aneurysm. The balloon remains inflated for a time sufficient to cause partial and/or complete solidification of the embolizing composition such that no protrusion and/or migration results. Next the delivery system is detached from the mass and the embolization procedure is complete.

E. Balloon Inflation/Deflation during Embolization

This technique enables the containment of an embolic material within an aneurysm during solidification or set-up and facilitates the extraction of any solvent and/or the interaction between the embolic agent located at the neck (i.e., opening) of the aneurysm and blood. A flow arresting device such as a balloon is employed to facilitate the extraction of a solvent and/or the interaction between the embolic agent and blood. In addition, the interaction between the balloon and the delivery system is important. Namely, the delivery system may have a tendency to become closed due to over inflation of the balloon. This methodology sets limits on the inflation of the balloon to guard against closure of the delivery system while still completely sealing the neck of the aneurysm.

Without being limited to any theory, it is believed that this technique seals the neck of the aneurysm while an embolic composition is delivered and facilitates the solidification of the agent by the creation of a high speed laminar type flow around the balloon to extract any solvent and/or induce contact with blood.

Testing revealed that a balloon diameter about 15% greater than arterial diameter (e.g., per compliant balloon) results in the substantially complete seal of the neck of the aneurysm while still being able to maneuver a guidewire and inject an embolic agent through the delivery system. It is expected that the diameter of the inflated balloon can typically range from about 100 to 130% of the inner diameter of the vessel. Secondly, testing revealed that a balloon diameter 85% of the parent artery inner diameter significantly increases the extraction of solvent injected into the aneurysm by washing the solvent downstream. It is expected that the diameter of the deflated balloon can typically range from about 10 to 90%. Hence the methodology results in an adequate seal of the neck of the aneurysm embolization and a method by which to facilitate the solidification of the embolic material at the neck of the aneurysm (the material most prone to protrusion and/or migration out of the aneurysm.)

Interface Needle

The interface needle addresses a problem of mixing between two liquids delivered through a catheter. The interface needle is particularly useful for creating a blunt interface between a biocompatible solvent and a liquid embolic composition which are delivered to the body for treating aneurysms, arterial venus malformations, head and neck tumors, tumors and peripheral applications.

Although the device is particularly suitable for creating a blunt liquid interface between the biocompatible solvent (dimethylsulfoxide-(DMSO)) and a biocompatible polymer composition, it should be understood that the systems and methods of the present invention may be used for creating a blunt liquid interface between any two liquids delivered sequentially through a delivery system.

The blunt liquid interface between the DMSO and a liquid embolic composition improves the delivery of the liquid embolic composition by allowing the formation of a small kernel or ball of polymer material during the initial injection, and preventing the formation of strands of polymer material which can be carried away in the bloodstream.

Figure 1:
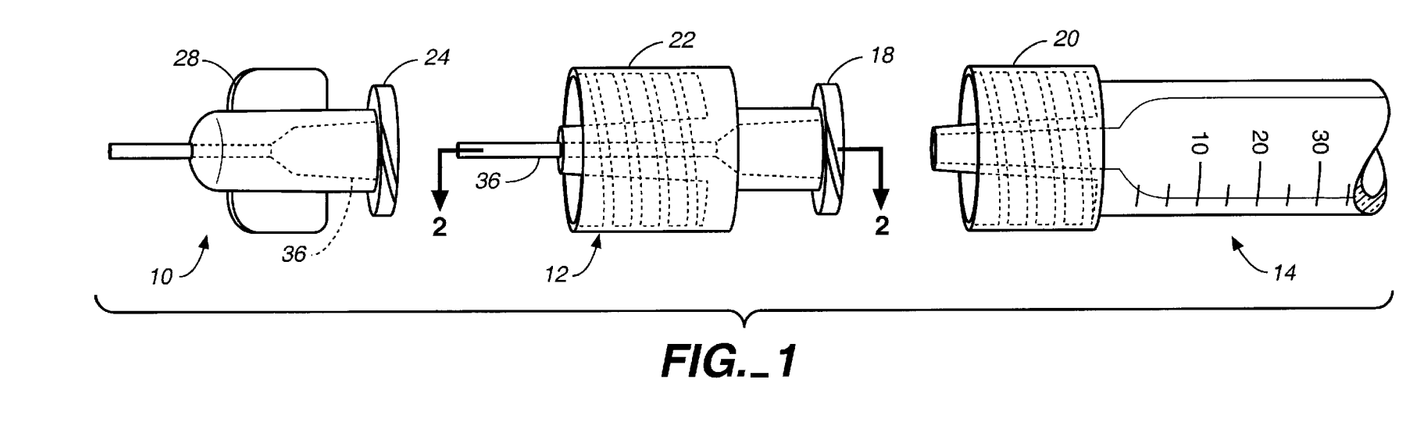
FIG. 1 is an exploded side view of a side view of a catheter, interface needle, and syringe system.

As shown in FIG. 1, the system for liquid delivery with a blunt liquid interface includes a catheter 10, an interface needle 12, and a syringe 14. The interface needle 12 includes a proximal end with a female luer fitting 18 for connection to a male luer fitting 20 of the syringe 14. A distal end of the interface needle 12 includes a male luer fitting 22 for connection to a female luer fitting 24 of a catheter hub 28.

Figure 2:
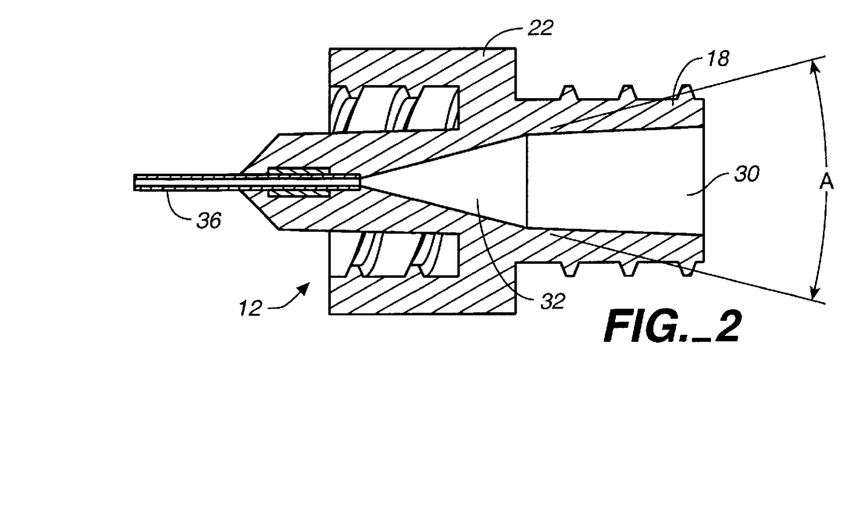
FIG. 2 is a cross sectional view of the interface needle, taken along line 2—2 of FIG. 1.
Figure 3:
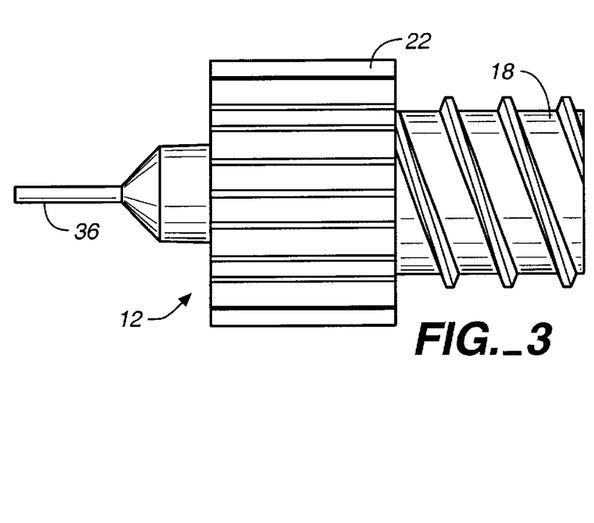
FIG. 3 is a side view of the interface needle.

As shown most clearly in the cross-sectional view of FIG. 2, the interface needle 12 includes a lumen 30 with a tapered portion 32. The tapered portion 32 tapers from a largest proximal dimension to a smallest distal dimension. The taper is provided at an angle A which is between about 10 and about 60 degrees, preferably between about 20 and about 40 degrees, and most preferably approximately 30 degrees. A hypo tube 36 is fitted within the lumen 30 and extends from the distal end of the male luer fitting 22. The hypo tube 36 may be overmolded, press fit, crimped in place, or otherwise secured inside the lumen 30 of the interface needle 12. The body of the interface needle 12 is preferably formed of a polymer material which is compatible with DMSO such as polypropylene, polyethylene, polyester, and the like. The hypo tube 36 extends from the distal end of the male luer fitting 22 a distance sufficient to allow the hypo tube to bypass a reservoir 36 in the catheter hub 28 and delivers the liquid directly into the catheter lumen. The length of the hypo tube 36 may vary depending on the type of catheter hub 28 used. For example, the hypo tube 36 may have a total length of about 0.2 to about 0.5 inches and a length extending from the distal end of the male luer 22 of about 0.05 to about 0.3 inches. The hypo tube 36 is dimensioned to fit within the lumen of the catheter 10 forming a seal between the interface needle and the catheter lumen and bypassing any liquid in the reservoir 36 of the catheter hub 28.

One procedure for delivering two liquids and achieving a blunt liquid interface is as follows. Initially, a first liquid is delivered directly to the catheter 10 with a syringe. The second liquid is then provided in a second syringe and the interface needle 12 is connected to the second syringe. Air is expelled from the interface needle 12 and liquid is preferably cleared from the distal tip of the hypo tube 36. The male luer fitting 22 of the interface needle 12 is then connected to the catheter hub 28 such that a blunt liquid interface is formed between a first liquid in the catheter and a second liquid in the hypo tube 36.

When the present invention is used to deliver a liquid embolic composition with a blunt or even interface between a biocompatible solvent and a liquid embolic composition, the procedure employed is as follows. The syringe 14 is filled with the liquid embolic composition and the interface needle 12 is attached to the syringe. Air is expelled from the interface needle 12 by injection of liquid embolic composition and the exterior of the interface needle is preferably cleaned. The interface needle is then attached to the catheter hub 28 of a catheter which has been previously flushed with DMSO or other biocompatible solvent. The liquid embolic composition is injected slowly to create a blunt liquid interface between the DMSO and liquid embolic composition and prevent dilution of the two fluids. The blunt liquid interface created by the interface needle travels down the length of the catheter to a delivery site with minimal mixing between the two liquids.

Other suitable interface needles are disclosed in U.S. patent application Ser. No. 09/574,392, filed concurrently, which application is entitled, "Interface Needle and Method for Creating a Blunt Interface between Delivered Liquids." This application is incorporated herein by reference in its entirety.

Threaded Syringe

A preferred syringe that provides a mechanism by which a clinician can deliver a viscous fluid through relatively small lumens and can obtain tactile or audible feedback of delivery is preferred. The syringe can be used either as a conventional syringe or as a threaded syringe. The threaded syringe allows for delivery of more viscous fluids with less force and/or allows for more controlled delivery.

Figure 4:
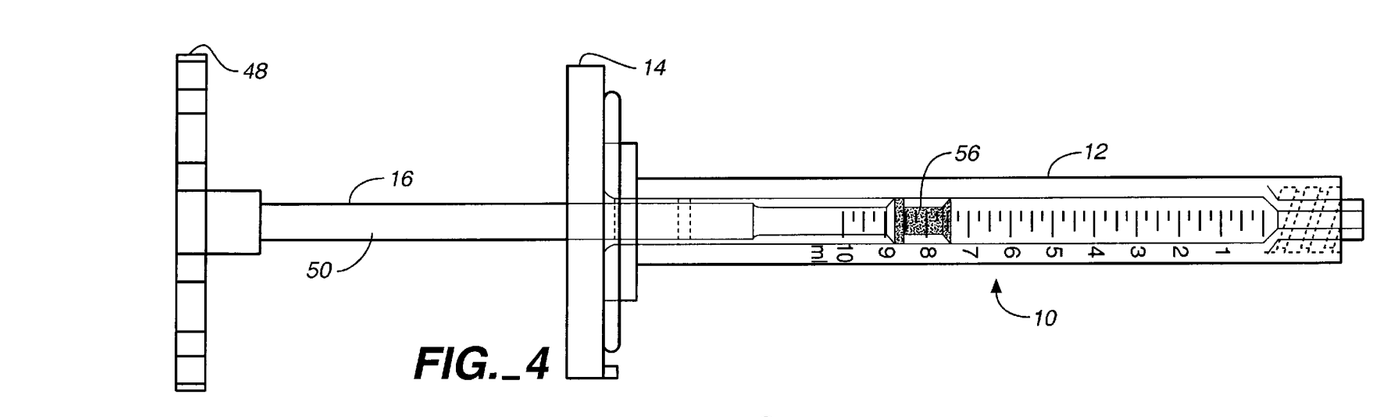
FIG. 4 is a side view of the syringe according to the present invention.

FIG. 4 shows a syringe assembly 10 according to the present invention which includes a syringe barrel 12, a sliding member 14, and a threaded plunger 16. The syringe barrel 12, as shown most clearly in FIG. 5, includes a distal delivery orifice 18 having a male luer fitting 20 to facilitate connection to a catheter hub. A proximal end of the syringe barrel 12 is provided with a flange 22. An end view of the of the flange 22 is illustrated in FIG. 6A.

Figure 7:
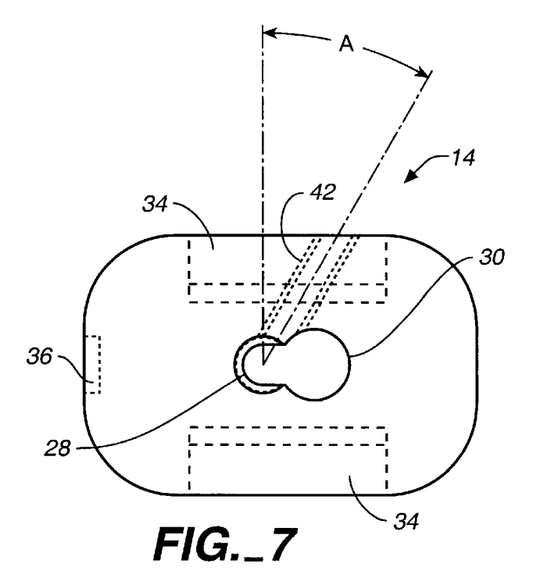
FIG. 7 is a is a top view of a sliding end member of the syringe.
Figure 8:
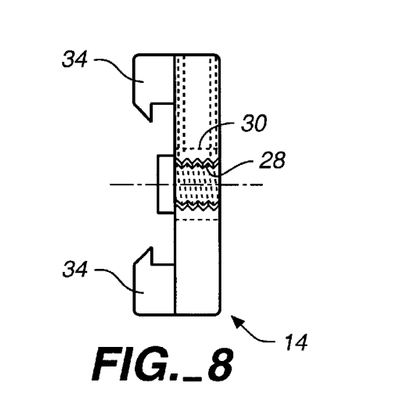
FIG. 8 is a side view of the sliding end member of FIG. 8.

The sliding member 14 is shown in further detail in FIGS. 7 and 8. The sliding member 14 includes a threaded through bore 28 and a second unthreaded bore 30 having a diameter slightly larger than that of the threaded bore 28. The sliding member 14 also includes side rails 34 and an end stop or tab 36. The sliding member 14 is received on the flange 22 of the syringe barrel 12 such that the flange is received between the side rails 34 of the sliding member and the sliding member can slide back and forth along the flange. The ability of the sliding member 14 to slide with respect to the barrel 12 allows either the threaded bore 28 or the unthreaded bore 30 to be axially aligned with the syringe barrel 12. Accordingly, the syringe can be used as a conventional syringe when the unthreaded bore 30 is aligned with the syringe barrel and can be used as a threaded syringe for a more precisely controlled fluid delivery when the threaded bore 28 is aligned with the syringe barrel 12.

Figure 9:
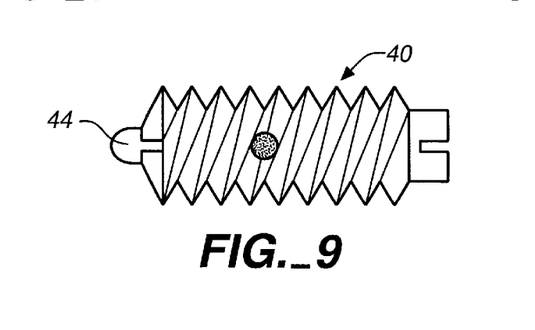
FIG. 9 is an enlarged side view of the spring element.

The sliding member 14 also includes a spring element 40 shown in FIG. 9 which is threaded into a side bore 42 in the sliding member. The side bore 42 is positioned at an angle A from a line which is transfers to the direction of sliding. The angle A is between about 10 and about 60 degrees, preferably between about 20 and about 40 degrees, and most preferably about 30 degrees. The spring element 40 includes a threaded casing which contains a spring and a movable ball element 44.

Figures 5, 6A, 6B:
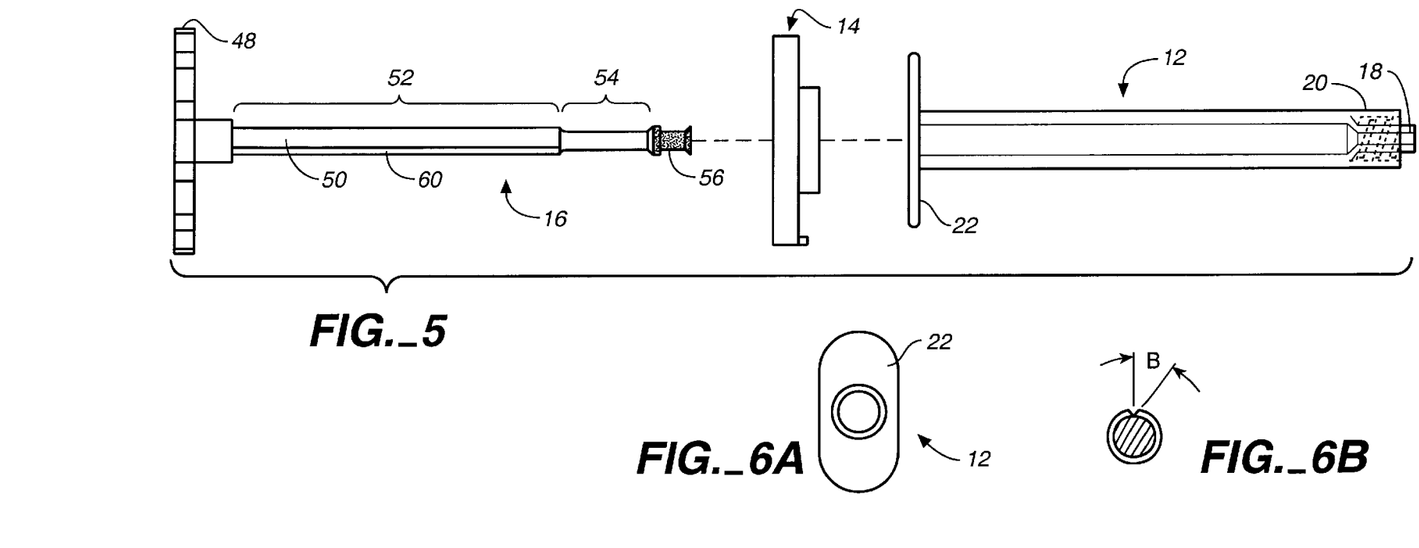
FIG. 5 is an exploded side view of the syringe of FIG. 4.
FIG. 6A is an end view of the proximal end of the syringe barrel.
FIG. 6B is an enlarged cross sectional view of the plunger shaft.

The threaded plunger 16 as shown in FIG. 5, includes a plunger handle 48 connected to a shaft 50. The shaft 50 includes a threaded portion 52 and an unthreaded portion 54. A distal end of the plunger 16 includes a resilient fluid tight member 56. The threaded portion 52 of the plunger is provided with a longitudinal groove 60 which cuts through the plunger threads as shown in FIG. 6. The longitudinal groove 60 is preferably a V-shaped groove which encompasses an angle B of about 30 to about 60 degrees, preferably approximately 90 degrees. The ball element 44 of the spring element 40 is configured to be received in the groove 60 of the threaded plunger 44. The inter-engagement of the spring element 40 and the longitudinal groove 60 provide a tactile and/or audible indication to the clinician. With the longitudinal groove 60 as shown in the drawings, the clinician will feel and/or hear a click of the syringe plunger 16 for each rotation of the plunger 16. Other arrangements of the groove 60 may be provided to provide a tactile or audible indication at frequencies other than one click per rotation. For example, every other thread may be provided with a transverse notch to provide tactile indications for every two rotations.

The syringe assembly 10 according to the present invention provides a mechanism by which the syringe can be filled with fluid in the normal fashion with the plunger shaft 50 positioned in the unthreaded bore 30 of the sliding member 14. After filling, the sliding member 14 can be slid to a second position at which the plunger shaft 50 is positioned in the threaded bore 28 and the threaded plunger is used for slow, controlled injection of fluid by rotation of the plunger. In order to slide the sliding member 14 from the first position to the second position, the plunger 16 should be positioned with the unthreaded portion 54 of the plunger shaft 50 located at the intersection of the bores 28, 30 in the sliding member 14. The groove 60 and spring element 40 provide a tactile and/or audible indication or click upon each revolution of the threaded plunger 16. This allows the clinician to determine the amount of fluid injected without looking at the syringe graduation lines.

U.S. Provisional Patent Application Serial Nos. 60/135, 289 and 60/135,287, entitled "THREADED SYRINGE" and entitled "SCREW SYRINGE WITH FORCE RELEASE MECHANISM" provide a further description of these devices. Both of these applications are incorporated herein by reference in their entirety.

Utility

The methods, devices, and compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, the invention finds use in human and other mammalian subjects requiring embolization of blood vessels.

It is contemplated that the compositions can be employed as a carrier for a compatible pharmaceutically active compound wherein this compound is delivered in vivo for subsequent release. Such compounds include by way of example only antibiotics, anti-inflammatory agents, chemotherapeutic agents, and the like.

The following example is set forth to illustrate the claimed invention and are not to be construed as a limitation thereof.

EXAMPLE

The following example illustrates one method for delivery of an embolic composition as per this invention. In this example, the following composition is employed:
- approximately 17.5 weight % EVOH
- 30 weight % micronized tantalum
- approximately 52.5 weight % DMSO
- Viscosity=approximately 1100 cSt at 40° C.

The composition is prepared by dissolution of the polymer at 50° C. in DMSO with stirring. Afterwards, micronized tantalum (average size 3 $\mu$m) is then added. The resulting composition is heated for about 5 minutes at 70° C. then shaken in a vortex mixer for approximately 20 minutes at room temperature to obtain a uniform suspension of the insoluble tantalum in the composition.

1.5 mL of the composition described above is employed in a sterile vial in conjunction with a 1 mL delivery syringe, one threaded syringe device with an interface device, a Rebar microcatheter available from Micro Therapeutics Inc., Irvine Calif. (105-5080), and an Equinox Balloon catheter available Micro Therapeutics Inc., Irvine Calif. The composition must be used with appropriately designed DMSO compatible microcatheters and balloon catheters.

The composition is injected into an aneursym as follows:

1. The vial comprising the embolic composition is heated dry at 70° C. for 5 minutes then shaken for 20 minutes on a suitable mixer. The mixing is continued with intermittent heating per step 6 until ready to be injected into the catheter.
2. Confirm microcatheter placement in upper third (⅓) of aneurysm sac with injection of contrast agent.
3. Confirm balloon placement, inflation volume and neck coverage by inflating balloon. Record volume of balloon inflation for use during this embolization. Balloon inflation should be carefully conducted since over inflation of balloon catheter may cause occlusion of delivery catheter leading to over pressurization.
4. With the balloon deflated, flush contrast from microcatheter with 5 ml of saline. Leave the syringe connected.
5. Fill microcatheter deadspace: aspirate approximately 0.8 mL of sterile DMSO into a 1 mL syringe. Inject the DMSO into the delivery microcatheter in sufficient volume to just fill the catheter deadspace at a rate not greater than 0.3 mL/min and preferably not greater than 0.1 mL/min.
6. Ensure that the embolic composition is mixed per step 1. Fill a 1 mL threaded syringe with the mixed embolic composition through a 16 or 18 gauge needle. Activate the syringe device to deliver 0.2 mL of the embolic composition to the catheter. Connect an interface device to the syringe. Turn syringe knob to inject embolic composition through the interface device and to remove air. As soon as the DMSO is injected into the catheter deadspace, remove the DMSO syringe and overfill and wash the luer hub with the balance of the DMSO.
   NOTE: The threaded syringe generates a tactile click for each full revolution. Each full revolution is equal to 0.02 ml.
7. Immediately connect the embolic composition threaded syringe/interface device to the microcatheter hub, making sure there is no air in the hub during the connection. Failure to continuously mix embolic composition for the required time may result in inadequate fluoroscopic visualization during delivery.

8. Inject 0.2 ml maximum of the embolic composition into the microcatheter at a steady rate not to exceed 0.1 ml/min. (Balloon deflated). Rapid injection of DMSO into the vasculature may lead to vasospasm and/or undesired angionecrosis.
9. Wait one minute for DMSO to disperse from aneurysm sac.
10. Inflate balloon to same volume as determined in step 3.
11. Inject embolic composition through the microcatheter at a rate of 0.1 ml/min. Continue until up to 0.2 ml maximum has been injected, but for no longer than two minutes. If the embolic composition does not appear after 2 full revolutions of the syringe handle, stop injection and replace catheter. Excessive pressure may result in catheter rupture. Maximum quantity and time of injection of the embolic composition should be reduced to be proportional to amount of fill desired in each injection. Aneurysm size should be considered for each injection.
12. Allow the balloon to stay inflated for a total of five minutes. (To allow for solidification of the embolic composition). Then completely deflate balloon to reestablish perfusion.
13. Repeat steps 10–12 until fill is completed.
14. Upon completion of injection allow ten (10) minutes for solidification (Balloon deflated). Aspirate syringe at least 0.25 ml during ten minute solidification period. Aspirating will allow for pressure in column to dissipate and prevent inadvertent injection of the embolic composition during separation.
15. Remove slack from catheter and quickly pull the catheter to separate the catheter from the precipitated mass.
16. Remove balloon system.

From the foregoing description, various modifications and changes in the above described methods will occur to those skilled in the art. All such modifications coming within the scope of the appended claims are intended to be included therein.

What is claimed is:

1. A method for embolizing a vascular site, comprising delivering, via a catheter, to said vascular site a composition comprising:
   (1) a biocompatible polymer;
   (2) a biocompatible water insoluble contrast agent; and
   (3) a biocompatible solvent,
   wherein said method comprises the following protocols, conducted during a single surgical procedure:
      (a) positioning the distal end of said delivery catheter in said vascular site, wherein said delivery catheter is connected to a source of said composition and whereby said composition can be injected into the vascular site through said delivery catheter;
      (b) positioning a flow-arresting device at said vascular site to be embolized;
      (c) activating the flow-arresting device at said vascular site to be embolized such that the activated device substantially arrests blood flow through said vascular site;
      (d) injecting said composition into said vascular site;
      (e) partially deactivating said flow-arresting device until is has a diameter of from about 10% to about 90% of said inner diameter of said vascular site to permit sufficient blood flow through said vascular site to be embolized, such that removal of said biocompatible solvent is facilitated and oxygenated blood is delivered to the tissue distal to said flow-arresting device; and
      (f) repeating protocols (c)–(e) at least once, and as necessary, to effect embolization of said vascular site.

2. The method according to claim 1, wherein protocol (c) comprises inflating said flow-arresting device so that said inflated flow-arresting device has a diameter that is greater than the inner diameter of said vascular site.

3. The method according to claim 2, wherein said flow-arresting device is inflated to a diameter that is about 100% to 130% of the inner diameter of said vascular site.

4. The method according to claim 1, wherein in protocol (e), the flow-arresting device is deactivated until its diameter is about 20 to about 25% of the diameter of said vascular site, allowing at least some of said biocompatible solvent to be removed from said vascular site, by entrapment in the body fluid.

5. A method for embolizing a vascular site, comprising delivering, via a catheter, into said vascular site a first embolic composition and then a second embolic composition, wherein each embolic composition comprises:
   (1) a biocompatible polymer,
   (2) a biocompatible water insoluble contrast agent, and
   (3) a biocompatible solvent,
   said method comprises the following protocols, conducted during a single surgical procedure:
      (a) positioning the distal end of said delivery catheter in said vascular site, wherein said delivery catheter defines a channel that contains said first embolic composition and said second embolic composition, wherein said first embolic composition is situated adjacent to said first embolic composition, and whereby each embolic composition can be injected into said vascular site through said delivery catheter, and wherein said first embolic composition has a higher concentration of biocompatible polymer or viscosity than said second embolic composition;
      (b) injecting said first embolic composition in said vascular site, whereby substantially no axial mixing of said first and said second embolic compositions occurs in said channel; and, thereafter;
      (c) injecting said second embolic composition into said vascular site.

6. The method according to claim 5, wherein protocol (b) comprises applying a first force into said channel to inject said first embolic composition into said vascular site, and wherein protocol (c) comprises applying a second force into said channel to inject said second embolic composition into said vascular site, wherein said first force is greater than said second force.

7. The method according to claim 5, wherein following protocol (b), said first embolic composition forms a nidus in said vascular site, and, following protocol (c), said second embolic composition forms a precipitate than emanates from said nidus, wherein said precipitate embolizes said vascular site.

* * * * *